United States Patent
Aminian et al.

(10) Patent No.: US 7,141,026 B2
(45) Date of Patent: Nov. 28, 2006

(54) BODY MOVEMENT MONITORING SYSTEM AND METHOD

(75) Inventors: Kamiar Aminian, Bussigny (CH); Bijian Najjafi, Lausanne (CH)

(73) Assignee: Ecole Polytechnique Federale de Lausanne/ Service des Relations Industrielles (SRI), Lausanne (CH)

( * ) Notice: Subject to any disclaimer, the term of this patent is extended or adjusted under 35 U.S.C. 154(b) by 39 days.

(21) Appl. No.: 10/398,462

(22) PCT Filed: Oct. 1, 2001

(86) PCT No.: PCT/CH01/00590

§ 371 (c)(1),
(2), (4) Date: Apr. 4, 2003

(87) PCT Pub. No.: WO02/28282

PCT Pub. Date: Apr. 11, 2002

(65) Prior Publication Data

US 2004/0015103 A1    Jan. 22, 2004

(51) Int. Cl.
   *A61B 5/103*   (2006.01)
   *A61B 5/117*   (2006.01)
(52) U.S. Cl. .................................................. 600/595
(58) Field of Classification Search ......... 600/587–595
   See application file for complete search history.

(56) References Cited

U.S. PATENT DOCUMENTS

| | | | |
|---|---|---|---|
| 5,125,412 A * | 6/1992 | Thornton | 600/483 |
| 5,337,758 A * | 8/1994 | Moore et al. | 600/595 |
| 5,919,149 A | 7/1999 | Allum | |
| 6,059,576 A * | 5/2000 | Brann | 434/247 |
| 6,095,991 A * | 8/2000 | Krausman et al. | 600/595 |
| 6,165,143 A * | 12/2000 | van Lummel | 600/595 |
| 6,659,968 B1 * | 12/2003 | McClure | 600/595 |
| 2003/0139692 A1 * | 7/2003 | Barrey et al. | 600/595 |

FOREIGN PATENT DOCUMENTS

| EP | 0 849 715 | 6/1998 |
|---|---|---|
| GB | 2 330 912 | 5/1999 |

OTHER PUBLICATIONS

Kerr et al, "Analysis of the sit-stand-sit movement cycle in normal subjects", Clinical Biomechanics, vol. 12, No. 4, Jul. 1, 1997, pp. 236-245.

Aminian et al, "Physical activity monitoring based on accelerometry: validation and comparison with video observation", Medical & Biological Engineering & Computing, vol. 37, No. 3, May 3, 1999, pp. 304-308.

* cited by examiner

*Primary Examiner*—Max F. Hindenburg
*Assistant Examiner*—Jonathan Foreman
(74) *Attorney, Agent, or Firm*—Nixon & Vanderhye, PC

(57) ABSTRACT

The present invention relates to a system and a method for monitoring body movement, in particular but not exclusively for evaluating the falling risk and/or for monitoring sitting, standing, lying, walking and running periods. The system is characterized by the fact that it comprises means for determining the time of postural transition.

10 Claims, 17 Drawing Sheets

(a)

(b)

BODY MOVEMENT MONITORING SYSTEM AND METHOD

This application is the US national phase of international application PCT/CH01/00590 filed 1 Oct. 2001 which designated the U.S.

The present invention relates to a system and a method for monitoring body movement, in particular but not exclusively for evaluating the falling risk and/or for monitoring walking or running periods.

Falls are certainly the most common type of home accidents among elderly people and are a major threat to their health and independence. Studies have shown that in a sample of community-dwelling persons of 75 years and older, 32% fall at least once a year. Among them, 24% sustain serious injuries. In addition, falling can dramatically change an elderly person's self-confidence and motivation, affecting his ability to function independently. Considering the growing part of very old people in the population of industrial countries (more than 47% of the elderly will be aged over 75 in 2006), falls will be one of the major problems of this important part of population.

Evaluating the risk of falling is important because it allows better providing adapted assistance and preventive measures to the concerned subjects. The risk of falling is generally evaluated by using a questionnaire that deals with problems of subjectivity and limited accuracy in recall or by clinical and functional assessment including posture and gait, independence in daily life, cognition and vision.

Nyberg and Gustafson ("Patients falls in stroke rehabilitation. A challenge to rehabilitation strategies," Stroke, vol. 26, pp. 832–842, 1995) reported that many falls in stroke patients occur during activities in which they change position (e.g. standing up, sitting down, or initiating walking). Although there are some studies about the relation of postural transition duration with the risk of falls, the methods of investigation used have serious limitation since they consist in performing tests under the constraint of laboratory and instruments such as force-platform.

Quantifying daily physical activity is a determining factor for evaluating the quality of life of subjects with limited mobility, e.g. in old age. Operative procedures and pathology, such as joints dysfunction and cardiovascular impairment, limit the patient's mobility and physical activity. A reliable measurement of the physical activity in everyday life would allow a better assessment of the utility and the relevance of a number of medical treatments. Continuous 24-h recordings of posture and motion can be generally useful in behavior assessment. The nature of postural transitions between standing, sitting and lying allow to categorize the type of activity and also to better understand problems occurring during daily activity (difficulty during rising from a chair, falling, etc,). The ability to sit and to stand may also be regarded as a physiologically essential function in human beings and a prerequisite for gait. In the past, the ambulatory measurement of physical activity often relied on the use of an accelerometer strapped on the waist, the wrist, or the ankle (see e.g. Patterson S. M., Krantz D. S., Montgomery L. C., Deuster P. A., Hedges S. M. and Nebel L. E., "Automated physical activity monitoring: validation and comparison with physiological and self-report measures", Psychophisiology, Vol. 30, pp. 296–305, 1993. NG A. V. and Kent-Braun J. A., "Quantitation of lower physicalactivity in persons with multiple sclerosis", Med. Sci. Sports Exerc., Vol. 29, pp. 517–523, 1997), but these methods provide no information on the type of activity. Recently new systems have been developed to identify the type of activity (K. Aminian, Ph. Robert, E. E. Buchser, "Physical activity monitoring based on accelerometry: validation and comparison with video observation", Medical & Bio. Eng. & comp, vol. 37, pp. 1–5, March 1999), but these methods are based on two different sites of attachment and due to discomfort caused by sensors and cable fixation, in certain cases, are not easy to use during long term monitoring of physical activity.

The above cited problems are overcome in the present invention which concerns a body movement monitoring system comprising:
  a sensor to be attached to the trunk of a subject,
  processing means for deriving information from said sensor,
  display means for displaying said information to an operator,
wherein said system includes means for determining the time of postural transition.

Preferably the sensor comprises a miniature gyroscope.

In the present text, the expression "postural transition" is defined as the movement performed during a sit-stand or a stand-sit transition (e.g. rise up from the chair, sit down the chair).

In an embodiment of the invention, the system also includes means to determine the duration of postural transition. As shown hereafter such a configuration allows the estimation of falling risk from ambulatory monitoring and during the daily life in elderly subjects. This results in an improvement in their life quality.

In another embodiment of the invention, the system also comprises a vertical accelerometer. As shown further in the text this additional element allows the monitoring of a complete physical activity, namely the detection of body postures such as sitting, standing and lying together with walking or running state. It should be pointed out that all these detections are carried out by a single sensor attached to the trunk (preferably on the chest).

In another embodiment of the invention, the system also comprises alarm means which are activated when the quality of postural transition is behind a threshold. The quality of postural transition is assessed using three parameters, namely the average and standard deviation of postural transition duration and the occurrence of abnormal successive transitions.

The invention will now be described by way of examples using the following figures:
  FIG. 1 illustrates postural transitions
  FIG. 2 illustrates a basis function used for a wavelet analysis
  FIG. 3 shows a flow chart of the algorithm used in example A
  FIG. 4 represents a first view of the results of example A
  FIG. 5 represents another view of the results of example A
  FIG. 6 shows a comparison for different postural transitions with a reference system
  FIG. 7 illustrates a situation where several postural transitions occur immediately one after the other
  FIG. 8 represents the sensors attachment in examples A and B
  FIG. 9 shows a vertical displacement (a) and the corresponding acceleration (b for sit-stand and c for stand-sit) in example B
  FIG. 10 illustrates the wavelet algorithm used with example A and B
  FIG. 11 shows the efficiency of the wavelet analysis FIG. 12 shows differently the efficiency of the wavelet analysis FIG. 13 shows a comparison between our sensor (Gyroscope) and a reference system (Vicon™).

EXAMPLE A

Falling Risk Evaluation in Elderly

METHOD

A. Experimental Design

Figure 1:
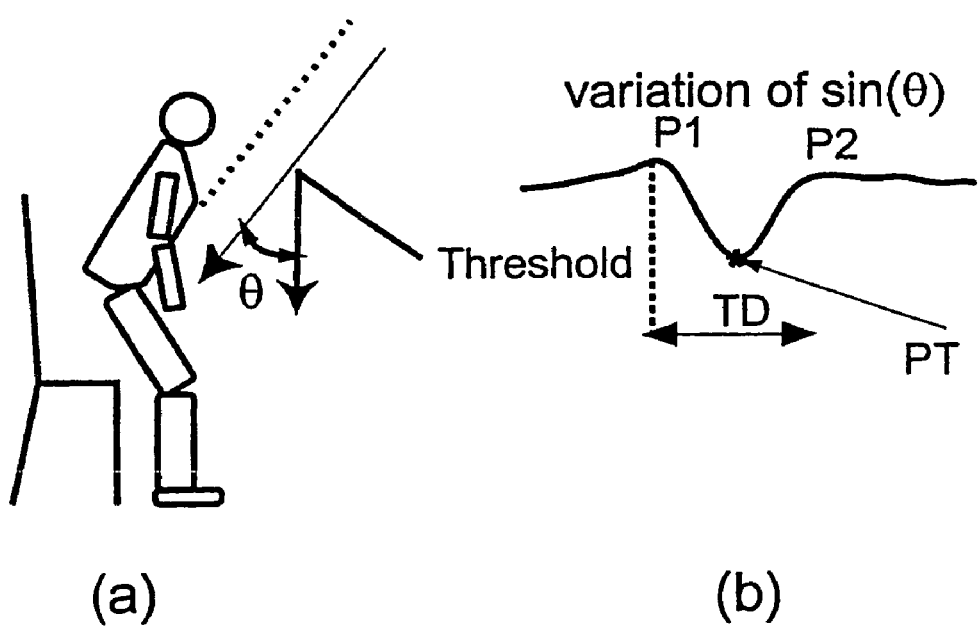

Eleven subjects older than 65 were studied. Written informed consent was obtained from all the subjects, and the ethical committee of the University of Geneva approved the protocol. A medical history was obtained including medication use and history of falls during the preceding year. A standardized mobility assessment testing static equilibrium and gait was performed according to Tinetti (M E Tinetti, T F. Williams, R. Mayewski, "Fall risk index for elderly patients based on number of chronic disabilities," Am. J. Med., vol. 80, pp. 429–434, 1986). A fall risk score was obtained by addition of subscores of known risk factors for falls, shown in table 1.

The final score was normalized between 0 (lowest risk) and 10 (highest risk). Subjects were divided into two groups: fallers and non-fallers. If a patient had fall risk score higher or equal to '5', he was classified as faller and else non-faller.

Each subject performed different activities involving postural transitions (such as Stand-Sit: SiSt, Sit-Stand: StSi) and dynamic activities (walking) with use of different type of chairs (standard wood chair, armchair and upholster chair) with and without use of armrest. The protocol of the measurement is presented in table 1. For each test, the subjects were asked to sit down and stand up three times.

TABLE 1

FALL RISK SCORE

| Parameters | Score |
| --- | --- |
| History of falls in the preceding year | No = 0/Yes = 2 |
| Static equilibrium disturbances | No = 0/Discrete = 1/Marked = 2 |
| Gait disturbances | No = 0/Discrete = 1/Marked = 2 |
| Troubles of vision | No = 0/Discrete = 1/Marked = 2 |
| Troubles of cognition | No = 0/Discrete = 1/Marked = 2 |
| Troubles of mood | No = 0/Discrete = 1/Marked = 2 |

TABLE 2

DIFFERENT TESTS PERFORMED BY EACH SUBJECT

| Test | Type of Activity | Type of Seat |
| --- | --- | --- |
| 1 | Sit to Stand + walking + Stand to Sit | Upholster without armrest (Seat Height: 48 cm) |
| 2 | Sit to Stand + Stand to Sit | Armchair with armrest (Seat Height: 46 cm) |
| 3 | Sit to Stand + Stand to Sit | Wooden chair without armrest (Seat Height: 46 cm) |
| 4 | Sit to Stand + Stand to Sit | Upholster chair without armrest (Seat Height: 48 cm) |
| 5 | Sit to Stand + Stand to Sit | Wooden Chair with armrest (Seat Height: 46 cm) |

B. Portable Measuring Device

Trunk tilt needs to be recorded for the successful identification of body posture transition. This trunk tilt corresponds to the angle 'θ' between the vertical axis and the subject's anterior wall of his thorax. In order to estimate θ a piezoelectric gyroscope (Murata, ENC-03J, ±400 deg/sec) was attached with a belt in front of the sternum. The angular rate signal was amplified, low-pass filtered (17 Hz), digitized (12 bit) at a sampling rate of 40 Hz by a portable data logger (Physilog, BioAGM, CH) and stored on a memory card. At the end of the recording the data were transferred to the computer for analysis.

C. Reference Method

A standard motion analysis system (Vicon™, Oxford Metrics, UK), was used as reference. Five infrared cameras arranged around the subject and four retro reflective markers placed one on the left acromion, one on the sternum manubrium and 2 on the belt holding the kinematic sensor, on each side of it. These markers have allowed an accurate 3D measurement of the chest movement. Trunk tilt and displacement of the gyroscope were calculated from the 3D components of the markers. The sample frequency of the recording was 50 Hz.

D. Postural Transition Estimation

FIG. 1 shows that during both SiSt and StSi transition, there is first a leaning forward followed by a leaning backward. In order to estimate the time of postural transition: PT, first the trunk tilt, 'θ', was calculated by integrating the angular rate signal measured by the gyroscope. Then the $\sin(\theta)$ was calculated and its minimum peak was considered as PT. The postural transition duration: TD, was calculated by estimating the interval time between the beginning of leaning forward and the end of the leaning backward. The estimation consisted to detect the maximum peaks before and after PT. Considering these two peaks respectively by $P_1$ and $P_2$, and their corresponding time by $t(P_1)$ and $t(P_2)$, TD was estimated as follow:

$$TD = t(P_2) - t(P_1)$$

E. Wavelet Analysis

Figure 2:

One of the drawbacks of integration from piezoelectric gyroscope is the presence of drift in the measured signal. In order to cancel this drift and to prevent other noises such as movement artifacts, which do not relate to posture transitions, discrete wavelet transform (DWT) based on Mallat algorithm was used as filtering method. This new tool differs from the traditional Fourier techniques by the way in which they localize the information in the time-frequency plane. In particular, it allows trading one type of resolution for the other, which makes them especially suitable for the analysis of nonstationary signals such as human motion signals. In this method, it is possible to analyze the signal in both of the time and frequency domains. This is an important aspect to detect the desired band frequency related to body posture transition. In other words, the important aspect of trunk tilt signals is that the information of interest is often a combination of features that are well localized in time and frequency domains. This requires the use of analysis methods sufficiently versatile to handle events that can be at opposite extremes in terms of their time-frequency localization. Moreover, this method allows using a suitable basic function, which is more similar to the pattern trunk tilt during transition. An example of a basic function is given in FIG. 2 for various dilation factors. Each of these functions has similar basic shapes and cyclic variations.

A multi-resolution transform is used to approximate the signal with different resolutions. It consists to split a signal into high-scale (low-frequency components) called approximation and low-scale (high-frequency components) called the detail. The decomposition is iterated, with successive approximations (or details) being decomposed in turn, so the original signal is broken down into many lower-resolution components. At each decompositions scale the number of samples in the time domain is decreased by throwing away every second sample (down sampling with a factor of '2'). By considering the original signal s(n) (i.e. sinus of trunk tilt), the approximation of the signal at scale j=0 is $A_{2^0}s$ which corresponds to the original signal s(n). At each new decomposition the approximation and detail loss in resolution since at each scale 2 samples will be replaced by one. At scale j the $A_{2^j}s$ represents approximation of s(n) with a resolution of one sample for every $2^j$ samples of the original signal.

Mallat showed that using a suitable low-pass filter h, and a high-pass filter g, the approximate signal $A_{2^{j+1}}s$ and detail signal $D_{2^{j+1}}s$ can be further written as following:

$$A_{2^{j+1}}s = \sum_{k=-\infty}^{+\infty} h(2n-k) \cdot A_{2^j}s$$

$$D_{2^{j+1}}s = \sum_{k=-\infty}^{+\infty} g(2n-k) A_{2^j}s$$

The coefficients of h and g filter are associated with the shape of wavelet considered for the analysis. In this study, decomposition into 10 scales with the 'Coiflet order 5' wavelets has been used.

In addition these wavelets can be implemented very efficiently using standard decimated (or non-decimated) filter-bank algorithms.

F. Algorithm

Figure 3:
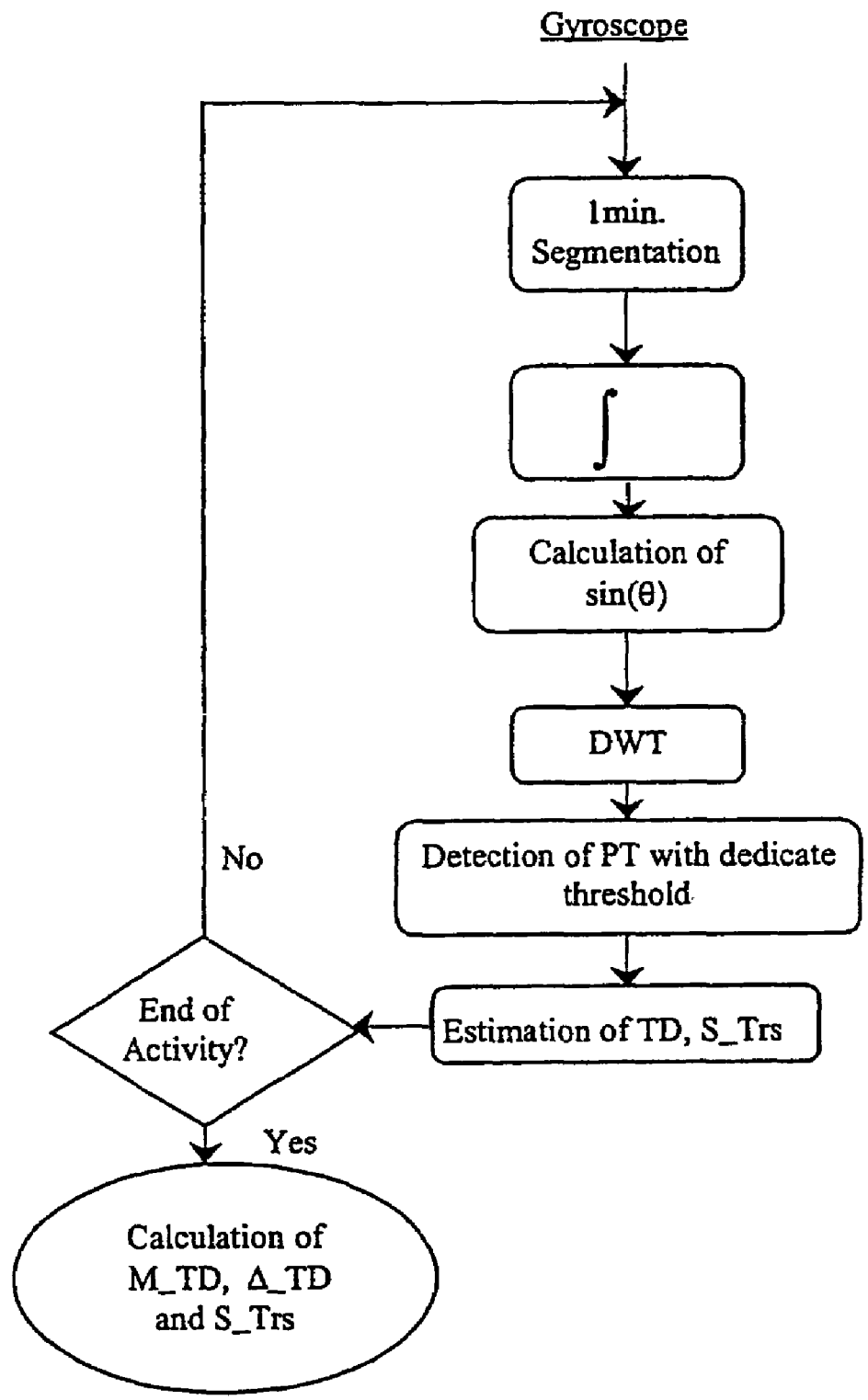

A flowchart of our algorithm is summarized in FIG. 3. First, signal of gyroscope was segmented to one-minute duration packs. Then the signal was integrated and $\sin(\theta)$ was calculated. In order to cancel the drift of integration and movement artifacts, wavelet analysis was applied. For each postural transition, the approximation corresponding to $(A_{2^k}s - A_{2^l}s)$ was chosen. The values of k and l correspond to scales, which provide the best approximation of StSi and SiSt transitions. PT and TD were estimated from $\sin(\theta)$ as described earlier. In the end of each test the mean of TD (M_TD) and its standard deviation ($\Delta$_TD) were calculated.

In order to test the significance of the TD for the evaluation of risk of falling, T-test was used between the parameters obtained for faller and non-faller groups.

Results

Figure 4:
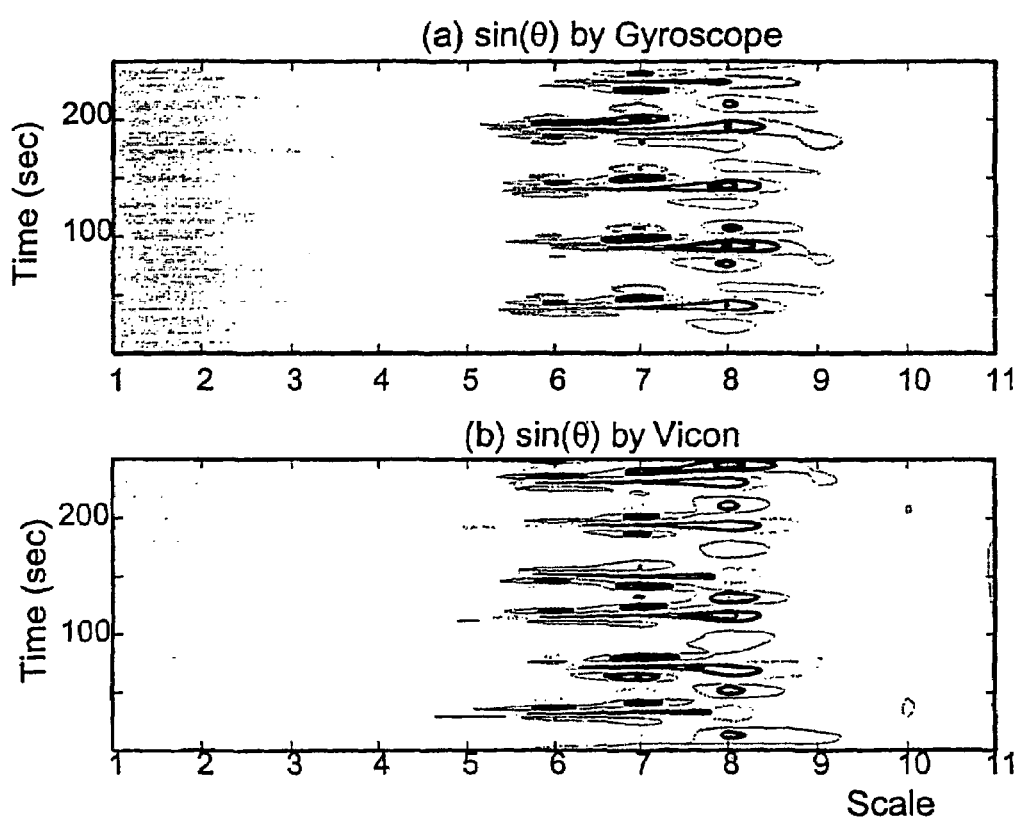

FIG. 4 shows the time-scale contour-plot of $\sin(\theta)$ obtained from the gyroscope compared to that measured with Vicon. The result shows that the best scale to extract relevant information correspond to the difference between course signals in scale k=5 and l=9 ($A_{2^5}f - A_{2^9}f$). This band frequency corresponding to 0.04–0.68 Hz was chosen for the DWT.

Figure 5:
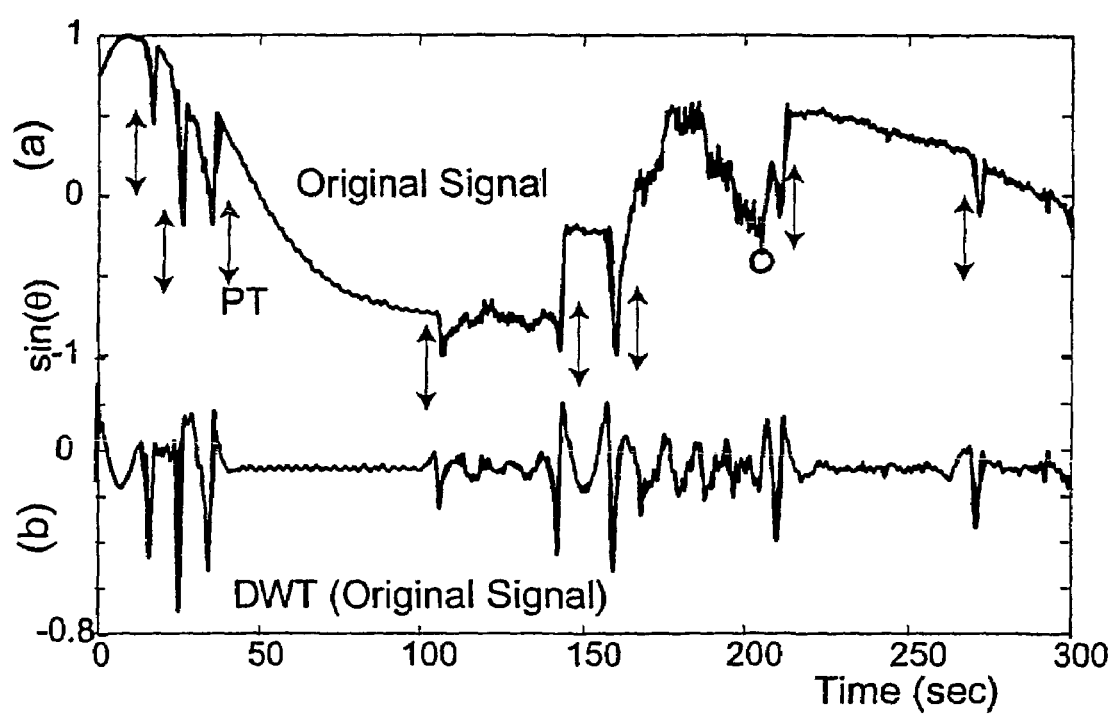

FIG. 5(a) shows a typical $\sin(\theta)$ obtained from the integral of angular rate rotation during several SiSt and StSi transitions. This figure shows a typical problem due to integration drift, which is canceled after DWT (FIG. 5(b)). In addition, superfluous peaks, which do not belong to transitions, can be observed in FIG. 5(a). These peaks were caused by movement artifacts during transition. In fact in some case, especially in subjects who have difficulty to rising from a chair, an oscillatory movement is superimposed on the measured signal. Since PT detection is based on peak detection, the presence of these peaks can produce some errors in transition detection. As shown in FIG. 5(b) these peaks were canceled by the DWT while the true transitions were significantly enhanced.

Figure 6:
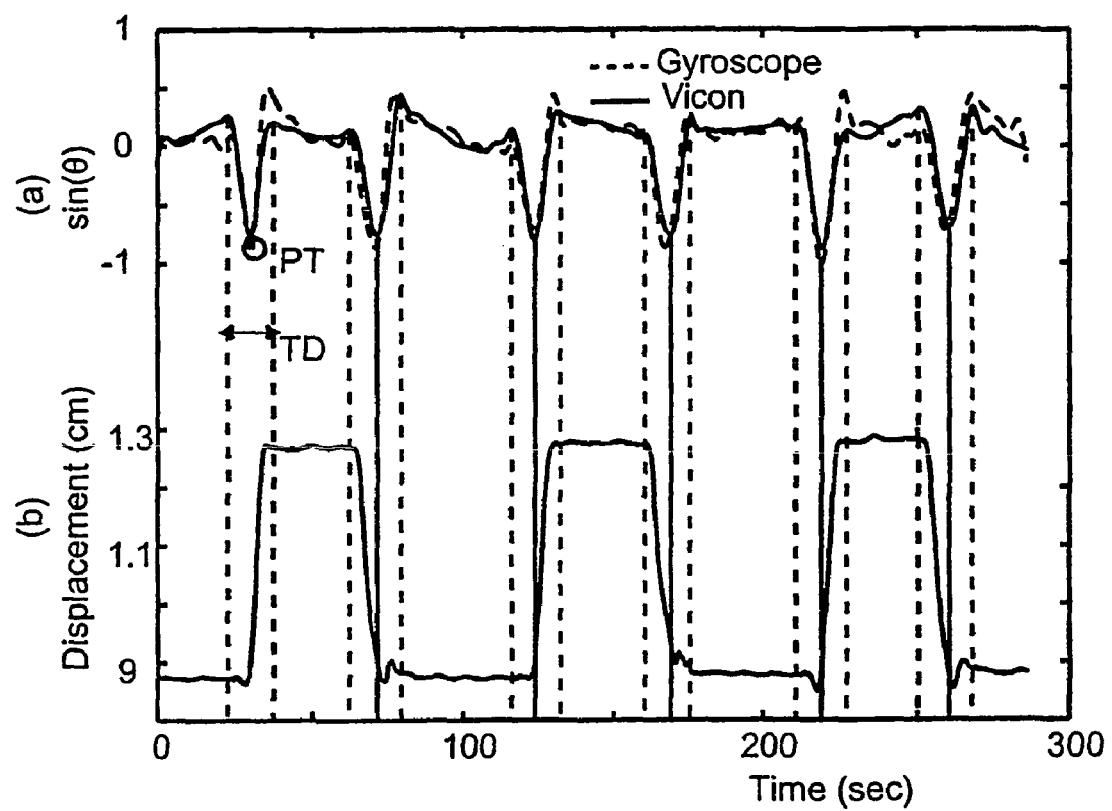

FIG. 6 compares for 6 postural transitions, a typical pattern of the displacement and $\sin(\theta)$ obtained with Vicon™ with $\sin(\theta)$ obtained from the gyroscope.

These results show that the estimated transition durations correspond to the true transition period observed with Vicon™. There is a close agreement between the two systems. The coefficient of correlation between $\sin(\theta)$ estimated from the gyroscope and that obtained from Vicon™ system varies between 0.90 and 0.99 depending on the performed test.

Table 3 shows for each subject the values of M_TD and $\Delta$_TD through all of the activities and the corresponding fall risk score. Expectedly, the non-faller group (fall risk score 0–3) was younger (75.5+/−3.39 years) than the faller group (fall risk score 5–10, 79.8+/−8.98 years).

TABLE 3

SUMMARY OF THE RESULTS PER SUBJECTS

| Subject | MTD_TD (sec) | $\Delta$_TD (sec) | S_Trs | Falling Risk Score |
|---|---|---|---|---|
| Faller | | | | |
| 1 | 3.85 | 1.343 | 14 | 10 |
| 2 | 4.97 | 1.665 | 5 | 9 |
| 3 | 3.27 | 1.018 | 5 | 8 |
| 4 | 4.16 | 1.262 | 0 | 5 |
| 5 | 3.17 | 0.930 | 0 | 5 |
| Non_faller | | | | |
| 6 | 3.24 | 0.593 | 0 | 0 |
| 7 | 2.96 | 0.576 | 0 | 0 |
| 8 | 2.92 | 0.549 | 0 | 1 |
| 9 | 2.94 | 0.729 | 0 | 1 |
| 10 | 2.52 | 0.371 | 0 | 3 |
| 11 | 3.14 | 0.959 | 0 | 2 |

Figure 7:
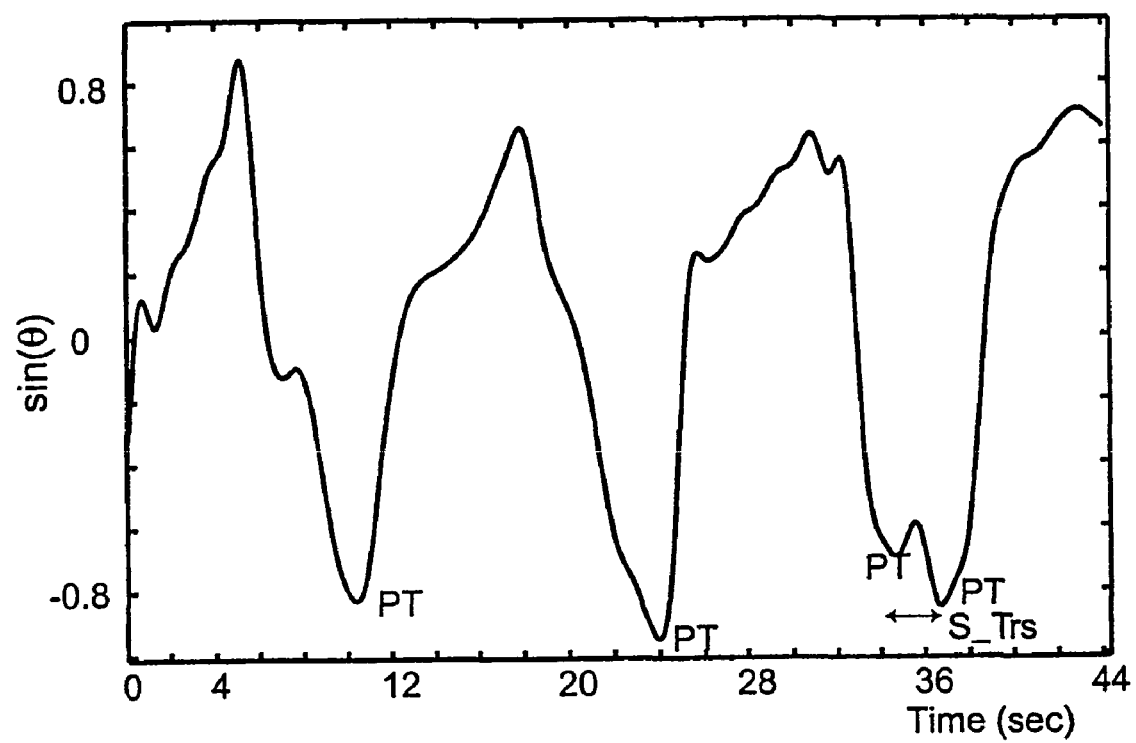

FIG. 7 shows a special case where several PTs occurring one immediately after the other while subject trying to stand or sit. This event called "successive transition" shows how many times a subject tries to make a PT but he/she unable to do it. The occurrence of "successive transition" is noted by S_Trs in the table 3. In fallers group, this parameter is increased with falling score while in non-fallers S_Trs is always null. T-test performed between fallers and non-fallers groups show a significant increase of M_TD (p<0.02) and $\Delta$_TD (p<0.002).

The above cited example has shown that, based on a simple model and an appropriate DWT, three parameters (i.e. M_TD, $\Delta$_TD and S_Trs) for evaluating the falling risk have been provided.

The comparison between the two groups of elderly subjects (i.e. fallers and non-fallers) shows that M_TD and $\Delta$_TD in different PT (whatever the type of chair) are significant parameters for discriminating between these two groups. In addition the occurrence of "successive transitions" is a third parameter, which is correlated to the fall risk score. These parameters correspond to one or two attempts before succeeding in standing up from a seat. These attempts due to muscular weakness or joint stiffness are indicative of a higher risk of falls during a very simple daily life activity. It is important to note that both normal and "successive transitions" have been accurately classified (sensitivity more than 99%).

The type of PT (i.e. SiSt or StSi) did not change significantly as regards TD, therefore seems to have no specific role in the evaluation of falling risk in our tests. Table 4 shows the values of TD corresponding to SiSt and StSi for fallers and non-fallers groups. Although M_TD and Δ_TD are significantly different for fallers and non-fallers groups, within each group these values do not change significantly (p>0.4) with the type of transition (StSi or SiSt). It is clear that, if the type of transition were important, an improvement of the method would be necessary in order to classify the type of the posture. This classification could be made for instance by adding a vertical accelerometer on body trunk.

Although the results presented in this example concern short recordings involving a limited number of PT, it is important to note that the system can be used for a long term monitoring. The batteries lifetime and memory card allows monitoring up to 24 hours. If necessary, the datalogger can be recharged quickly and memory card replaced for a new recording. Contrary to stationary system such as video motion analysis or force-plate system, the proposed system allows measurement outside of the laboratory, in ambulatory and daily life conditions. The system does not hinder the subject since only one miniature sensor is used that can be attached everywhere on the trunk and the recorder is very light. The integration of the sensor and the- recorder in a same module allows providing a system especially adapted for ambulatory instrumentation and tele-alarm systems.

By considering the values of the estimated parameters during each day and their change over repeated measurements, the device can be considered a promising tool in home health care of elderly by giving objective figures of mobility of old people either healthy or suffering from specific conditions. Additionally, this device can be considered as a tool for an objective assessment of the fall risk and its change in elderly subjects during rehabilitation programs.

TABLE 4

TEMPORAL POSTURAL TRANSITION PARAMETERS
FOR FALLERS AND NON-FALLERS GROUPS

| Temporal parameters | Faller | | non-Faller | |
| --- | --- | --- | --- | --- |
| | SiSt | StSi | SiSt | StSi |
| M_TD (sec) | 3.73 | 3.93 | 2.90 | 2.95 |
| Δ_TD (sec) | 1.06 | 1.05 | 0.47 | 0.54 |

EXAMPLE B

Physical Activity Monitoring

METHODS

A. Experimental Setup 11 elderly-Community dwelling subjects (6 females, 5 males, age 79±6 years) carrying a kinematic sensor on the chest performed 6 tests involving various postural transitions and dynamic activities (table 5). Written informed consent was obtained from the subjects. During walking, some subjects have used a cane. The kinematic sensor was composed of one miniature piezoelectric gyroscope (Murata, ENV-05A, ±400 deg/sec) measuring trunk angular velocity ($g_s$) in the sagittal plane and one miniature accelerometer (ADXL02, ±9g), measuring vertical trunk acceleration ($a_v$). The gyroscope, the accelerometer and their conditioning electronic were packaged in a very small box and attached on the chest. Signals were digitized at 40 Hz sampling rate and recorded by a light portable data logger (Physilog, BioAGM, CH) carried on the waist.

Figure 8:
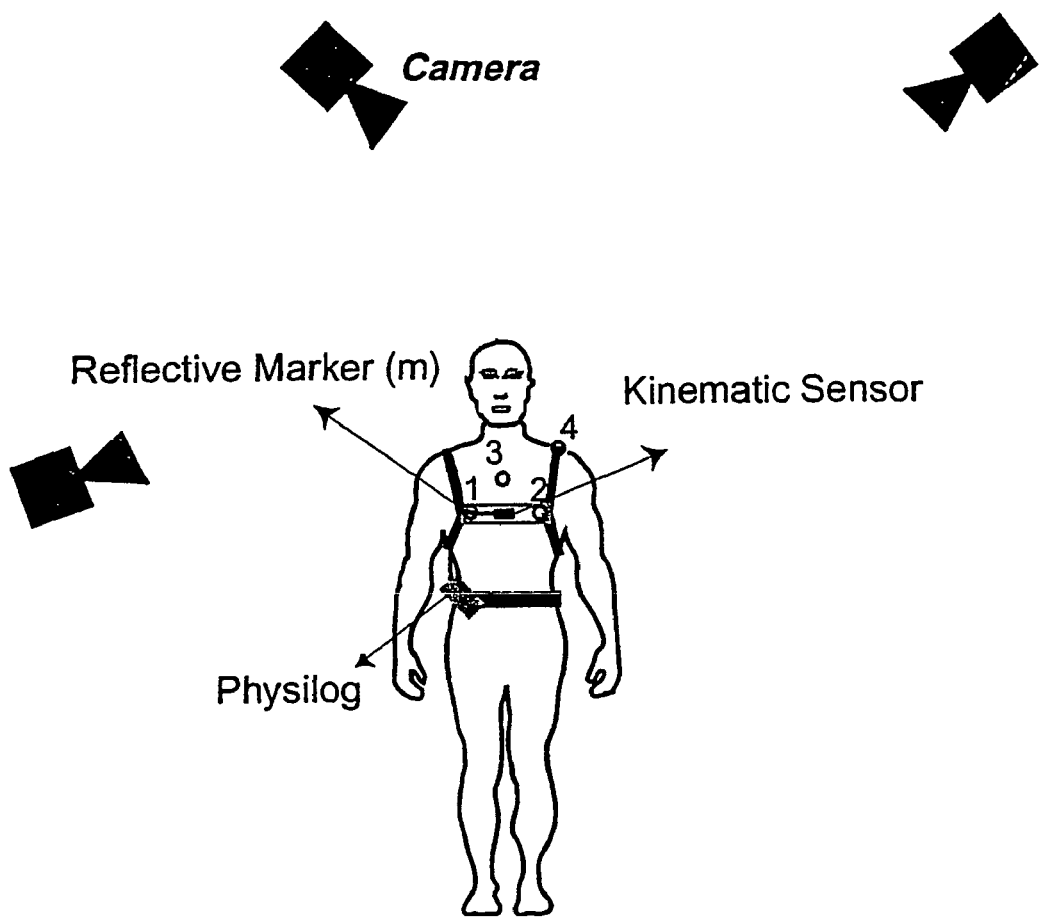

The results of each test were validated using 5 cameras and 4 retro reflective markers placed on the trunk (Vicon™, Oxford Metrics, UK). This optical system allows an accurate 3D capture of chest movement (FIG. 8). Three additional tests were performed with elderly subjects carrying the system for one hour in hospital building and outside, while an observer noted the actual activity of each subject.

B. Lying Detection

The recognition of the lying posture from sitting and standing was performed by considering the orientation of the accelerometer with respect to the direction of gravitational acceleration (vertical axis). In lying posture, the accelerometer measures almost zero g while in sitting and standing it shows around 1 g.

TABLE 5

DIFFERENT TESTS PERFORMED BY EACH SUBJECT

| Test | Type of Activity | Type of Seat |
| --- | --- | --- |
| 1 | Sit + Lying + Sit + Stand + walk | Bed (Desired Height for each subject) |
| 2 | Sit to Stand + walking + Stand to Sit | Upholster without armrest (Seat height: 48 cm) |
| 3 | Sit to Stand + Stand to Sit | Armchair with armrest (Seat height: 46 cm) |
| 4 | Sit to Stand + Stand to Sit | Wooden chair without armrest (Seat height: 46 cm) |
| 5 | Sit to Stand + Stand to Sit | Upholster chair without armrest (Seat height: 48 cm) |
| 6 | Sit to Stand + Stand to Sit | Wooden Chair with armrest (Seat height: 46 cm) |

C. Sitting and Standing Detection

Figure 9:
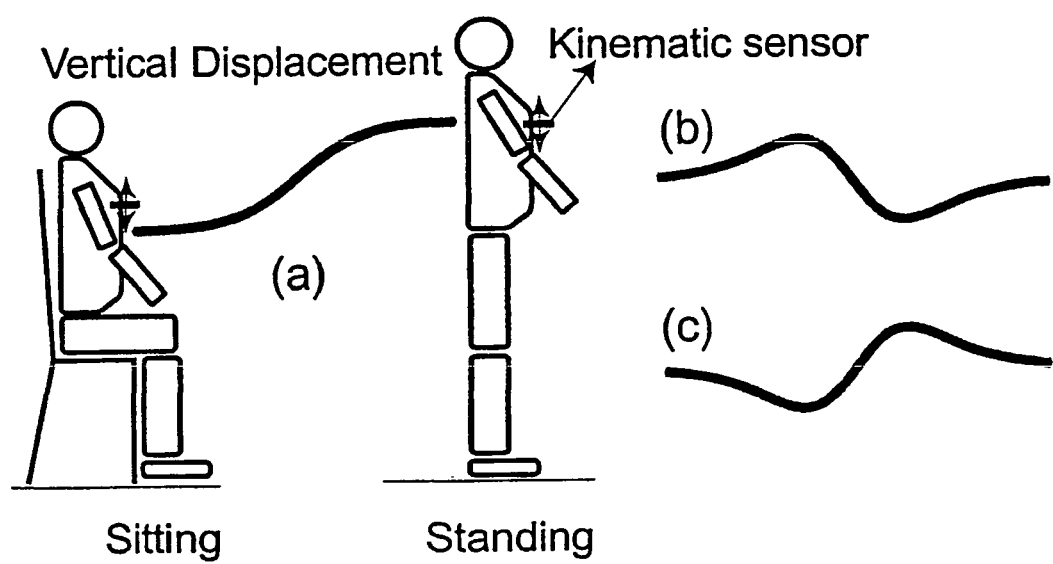

The main problem of posture discrimination concerns the separation of sitting and standing postures. Sitting occurs at the end of the stand to sit transition ('StSi') while standing occurs at the end of the sit to stand transition ('SiSt'). As a result, the identification of these two transitions is sufficient to recognize sitting and standing postures. The acceleration $a_v$ during SiSt (resp. StSi) transitions was described using a simple kinematic model. FIG. 1 shows that during both SiSt and StSi transition, there is first a forward lean followed by a backward lean. This tilt looks like a half period of sinusoid function where the minimum corresponds to the time of postural transition: PT. In order to estimate this time, first θ (the trunk angle in the sagittal plane) was calculated by integrating $g_s$. Then the sin(θ) was calculated and its minimum peak was considered as PT. The postural transition duration (TD) was calculated by estimating the interval time between the beginning of forward lean and the end of the backward lean. FIG. 9 shows, the nature of the vertical displacement during SiSt (also StSi) and the corresponding accelerations obtained from second derivative of the displacement. SiSt generates an acceleration peak (positive) followed by a deceleration peak (negative) while the inverse occurs for the StSi. Therefore, the pattern of $a_v$ during the TD can be used for SiSt and StSi estimation.

Figure 10:
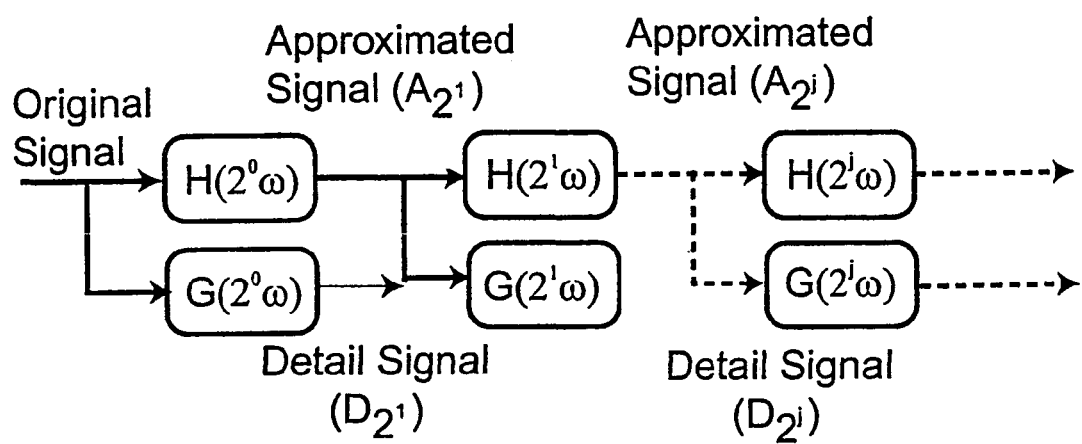

The important aspect of trunk tilt and acceleration pattern of posture transition is that the information of interest is often a combination of features that are well localized temporally or spatially. This requires the use of analysis methods sufficiently versatile to handle events that can be at opposite extremes in terms of their time-frequency localization. In trunk angular velocity, there are several peaks, which are not related to the posture transitions and make difficult the detection of the true pattern of PT. Moreover, computing θ from the integral of $g_s$ involves drift in the measured signal. In order to cancel the drift and to prevent other noises such as movement artifacts, which aren't related to posture transitions, Wavelet analysis based on Mallat algorithm was used. This algorithm is based on two dedicated filters H(ω) (Low-pass filter) and G(ω) (High-pass filter) has been presented in FIG. 10. At each scale j, the signal is divided into low frequency component (approximation: $A_2^j$) and high frequency component (detail: $D_2^j$) and loses in resolution because of downsampling. At scale j, $A_2^j$ represents the approximation of the original signal with a resolution of one sample for every $2^j$ samples of the original signal. In our algorithm, since all of the samples in time domain are needed, instead of down sampling in time domain the frequency band is divided by 2 in each step j. This new tool differs from the traditional Fourier techniques by the way in which they localize the information in the time-frequency plane. In particular, it allows trading one type of resolution for the other, which makes them especially suitable for the analysis of nonstationary signals such as human motion signals. Moreover, this method allows using a suitable basic function (mother wavelet), which is more similar to the pattern of trunk tilt and acceleration during posture transition. The approximation of $g_s$ between scales 5 and 9 ($A_2^5$–$A_2^9$) was used for TD detection. The band frequency corresponds to 0.06–0.45 Hz. The $a_v$ approximated signal between scales 5 and 6 ($A_2^5$–$A_2^6$) was used for SiSt or StSi recognition (band frequency: 0.34–0.68 Hz). For each approximation, 'coiflet' mother wavelet with order 5 was used.

D. Walking Detection

In order to detect the walking state, $a_v$ was analyzed every 5 seconds. Wavelet decomposition was also used to enhance the walking pattern and to reduce noise and drift arising from other activity such as posture transitions, turning or motion during standing posture. The approximated wavelet signal, DWT($a_v$), between scales 2 and 5 ($A_2^2$–$A_2^5$) was considered. A Daubechies mother wavelet with order 4 was applied. The band frequency corresponds to 0.68–5.47 Hz. For obtaining the pattern of walking, negative peaks beyond a fixed threshold were detected. Successive peaks agreeing a time difference of 0.25 to 2.25 s belong to walking step and were chosen as candidate peaks. We assumed that a true walking signature has at least 3 steps during each 5s interval. Then if more than three peaks were detected, these peaks were considering as walking steps.

E. Physical Activity Classification

By using the above algorithms physical activity was classified. However in order to improve this classification and reduce the false detection the following rules were considered:
  If two contradictory states were detected (e.g. lying with walking or sitting with walking), preference was given first to lying then to walking and finally to StSi or SiSt transition.
  Two successively SiSt (or StSi) detections were not considered as correct.
  Leaning backward during standing state was considered as inconsistent for elderly.

Results

Figure 11:
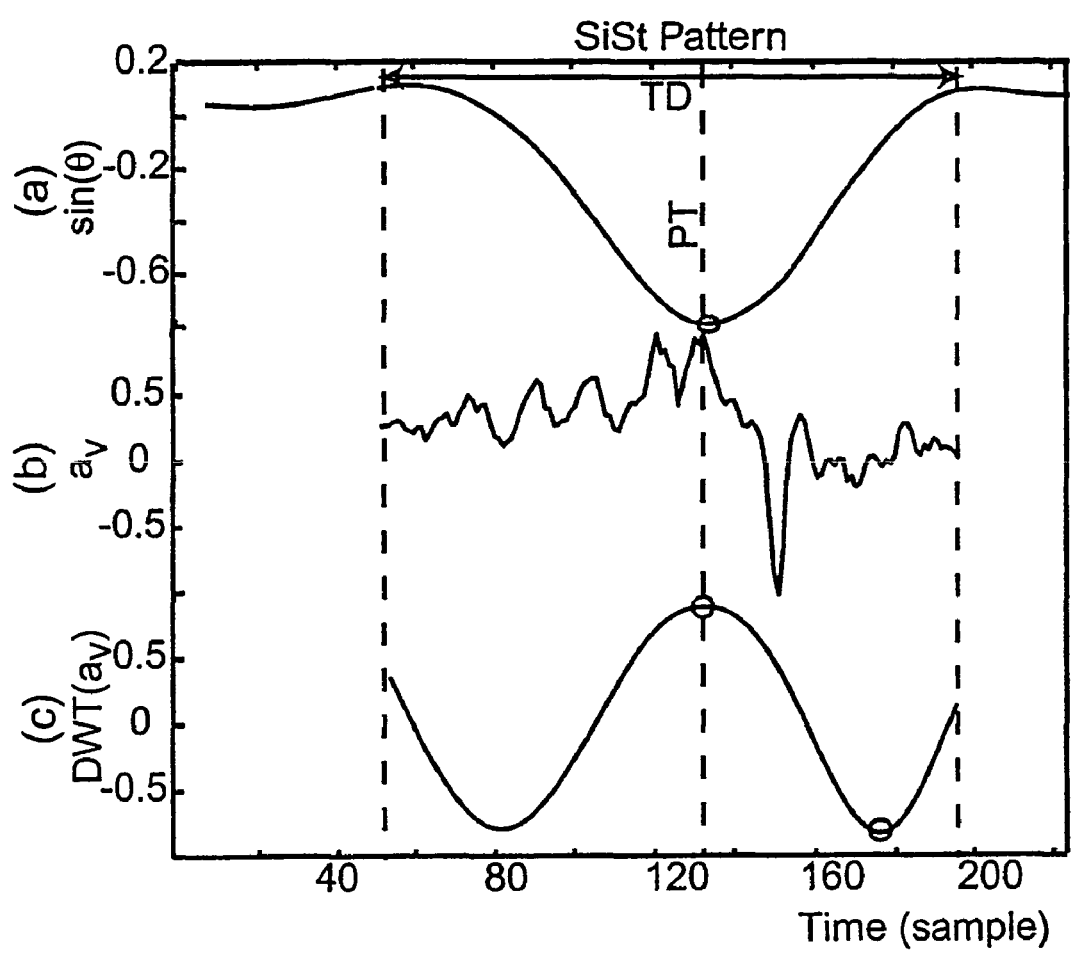
Figure 12:
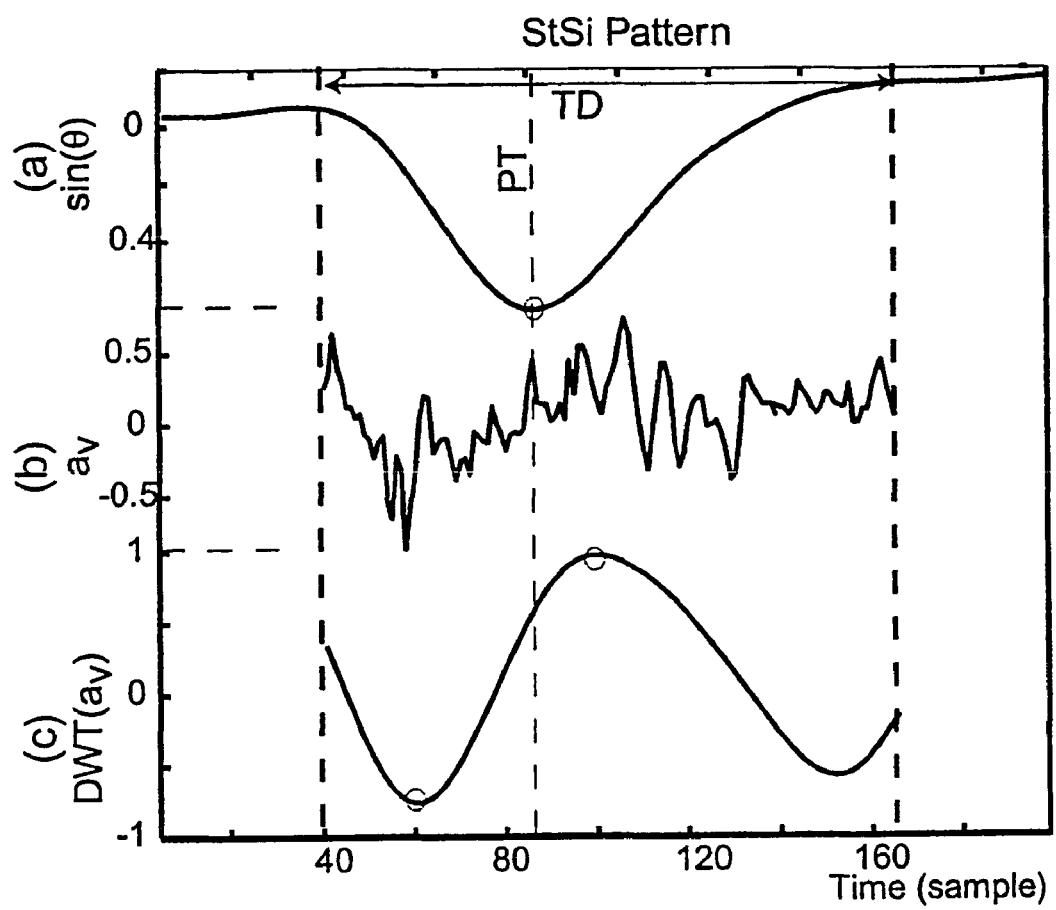
Figure 13:
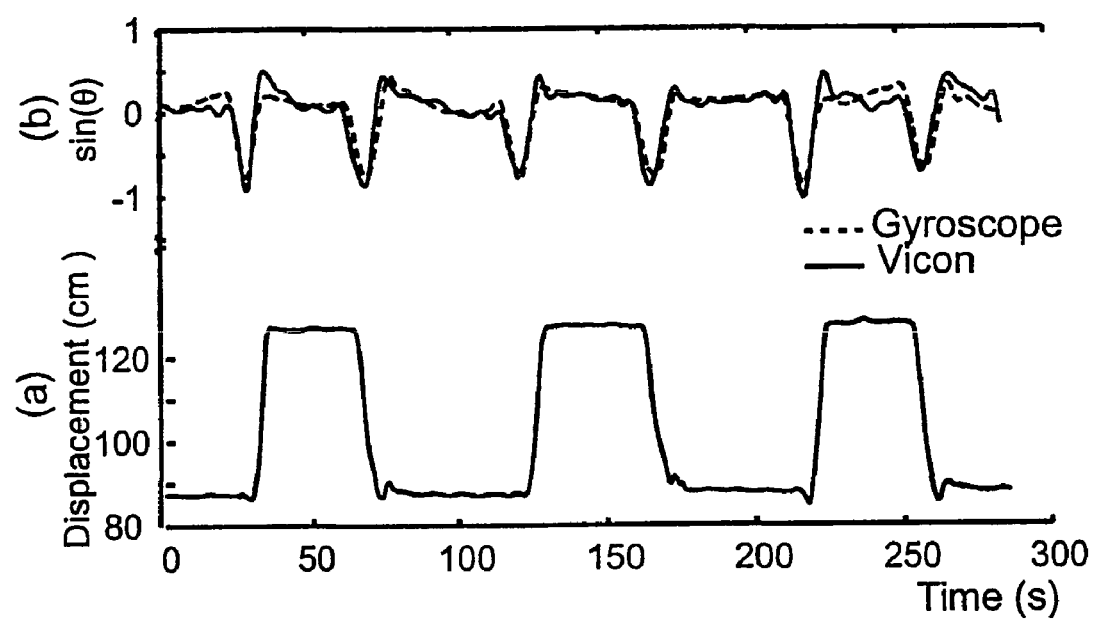

FIGS. 11 and 12 show the efficiency of the wavelet analysis for SiSt and StSi detection. As illustrated, the nearest peaks in DWT($a_v$) in respect to the local minimum of sin(θ) are correctly detected. Negative peak is followed by the positive one during SiSt transition (FIG. 11c) while the inverse occurs for StSi transition (FIG. 12c). The similarity of data obtained from the kinematic sensor and the Vicon™ system was high (0.90<r<0.99) as shown in FIG. 13. Among 287 postural transitions performed by all of the subjects, a sensitivity of 99% was obtained for detection of postural transition. The sensitivity and the specificity for sitting and standing classification have been shown in table 6. During tests 1 and 2, which involve walking and lying period, these parameters were more than 90%. In our tests all lying and getting-off from the bed periods were correctly classified.

Figure 14:
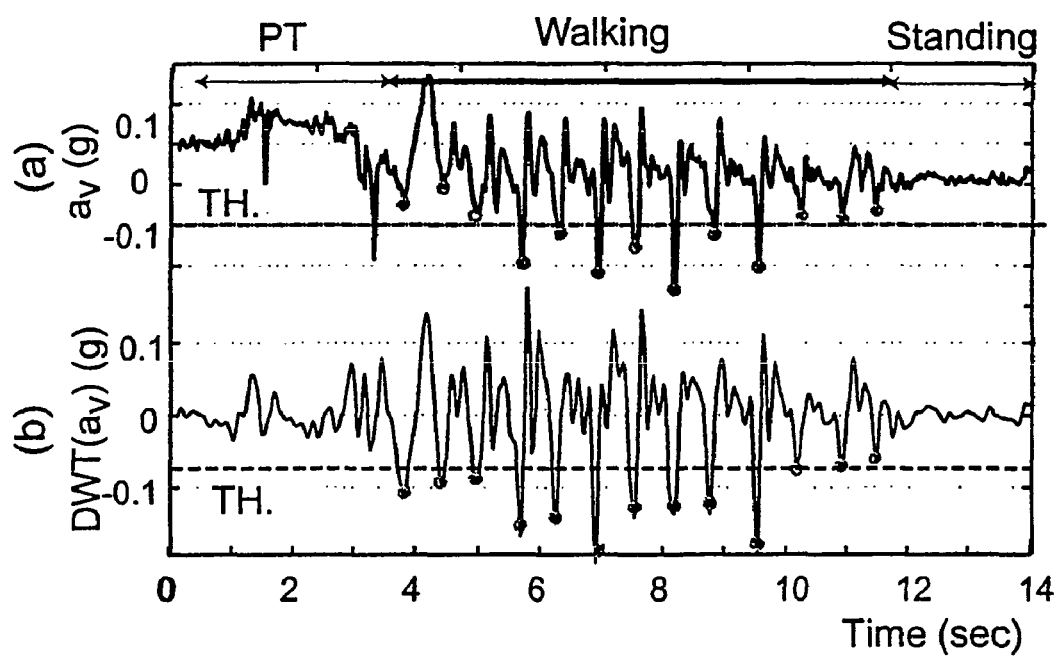
FIG. 14 shows the efficiency of the wavelet analysis for walking sequence enhancement.

FIG. 14 shows the effectiveness of wavelet analysis for walking sequence enhancement. In this figure, all peaks belonging to walking steps detected by the reference system (Vicon™) are marked. It can be seen that the drift in $a_v$ signal is reduced in DWT($a_v$) while the actual walking peaks have been enhanced, which let to a better peak detection.

These advantages of wavelet transform allow preventing any calibration for each subject. The sensitivity for walking period detection was more than 95%.

Figure 15:
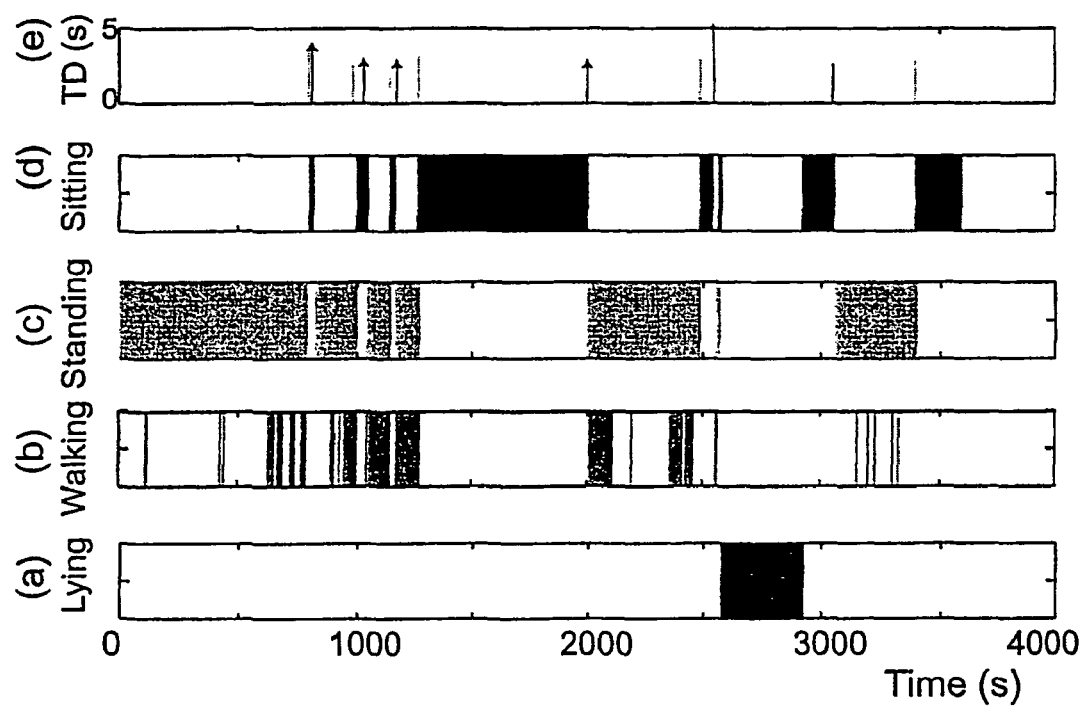
FIG. 15 shows a physical activity classification

FIG. 15 shows a typical physical activity classification obtained during one hour of recording for an elderly. In this test, there isn't any misclassification and the results correspond entirely to the observer notes. In two others tests performed during one hour with two other elderly, the sensitivity for detection of lying, SiSt, StSi and walking state were more than 90%.

This example has shown the possibility to categorize body postures and walking state with help of only one miniature sensor causing no discomfort for the subject. All results were validated using a standard reference system in a gait laboratory. The results show also that wavelet transform is a powerful technique to detect postural transition and to analyze walking pattern. The walking detection has a high sensitivity even, when subjects use walking aids such as cane. In addition, no calibration is needed according to each subject.

The results show that during the tests 3, 4, 5 and 6, which do not involve walking and lying, the sensitivity is lower than for the tests 1 and 2 where a period of walking or/and lying is included. This is essentially due to the correction made in PT from the walking and lying state detection. This confirm our assumption according to which in our classification, the priority is given first to lying then to walking and finally to StSi or SiSt. Furthermore during daily life, lying posture and specially walking state are often present.

TABLE 6

SENSITIVITY AND SPECIFICITY OF TRANSITION DETECTION

| Test Number | Total PT | Sensitivity % | | | | Specificity % | |
|---|---|---|---|---|---|---|---|
| | | PT | SiSt | StSi | Lying | Walking | SiSt | StSi |
| 1 | 40 | 100 | — | — | 100 | 95 | — | — |
| 2 | 65 | 97 | 91 | 97 | — | 97 | 97 | 94 |
| 3 | 58 | 100 | 83 | 83 | — | — | 86 | 86 |
| 4 | 52 | 98 | 54 | 77 | — | — | 80 | 54 |
| 5 | 56 | 100 | 54 | 89 | — | — | 81 | 58 |

TABLE 6-continued

SENSITIVITY AND SPECIFICITY OF TRANSITION DETECTION

| Test Number | Total PT | Sensitivity % | | | | | Specificity % | |
|---|---|---|---|---|---|---|---|---|
| | | PT | SiSt | StSi | Lying | Walking | SiSt | StSi |
| 6 | 56 | 100 | 75 | 86 | — | — | 80 | 77 |
| Mean | 57 | 99 | 71 | 86 | 100 | 96 | 85 | 74 |

This method offers a promising tool for long term and home care monitoring of daily physical activity. It may to better appreciating the quality of life of patients with disability by quantifying their degree of mobility. This system may also be used for assessment of risk of fall in elderly.

EXAMPLE C

Absolute Trunk Tilt Calculation

Estimation of forward trunk angle (tilt) can be useful for qualifying each activity. Finding of this parameter can be also useful for the correction of activity quality. For example having a correct angle can be important for facility of posture changing or having a successfully transition on the bed. Study about correlation of trunk tilt with lower member such as hip and leg is also useful for assessing the quality of body posture transition and could be considered as a falling risk parameter.

The measured frontal acceleration can be expressed as:

$$af_{acc.} = a_f \cos\theta + (a_v+g)\sin\theta \quad (1)$$

Where:
$af_{acc.}$=Measured signal by frontal accelerometer.
$a_f$=Inertial frontal acceleration
$a_v$=Inertial vertical acceleration
g=Gravity acceleration.
θ=Absolute angle (tilt) of body trunk surface (Place of sensor attachment).

For finding the absolute tilt, signal of accelerometer, which has been attached on body trunk surface in frontal direction, is analyzed. Measured signal by frontal accelerometer has two components consisting of frontal and vertical accelerations, which arise from inertial body movement and g×sin(θ), which arise from gravity acceleration (equation 1).

From equation 1, it is clear that when $a_f$=0 and $a_v$=0, the accelerometer signal is related to only absolute trunk tilt value ($af_{acc}$=g×sin(θ), if $a_f$=0 & $a_v$=0). In other word with measuring the acceleration signal in frontal direction in the situation of zero inertial acceleration, calculation of the absolute tilt will be possible. Moreover it can be assumed that the period where variance of $af_{acc}$ is lower than a dedicate threshold, $a_f$ and $a_v$ are around zero (g×sin(θ), has a zero variance since θ has around a constant value). Therefore the absolute tilt in case of no-movement (acceleration variance about zero) such as sitting, standing and lying in a rest state can be estimated by calculation of the sin(θ) from frontal accelerometer. For estimation of absolute tilt value in other case (activity with high variance), gyroscope signal is used as follow:

$$\theta = \int_{t_0}^{t} G\,dt + \theta(t_0) \quad (2)$$

Where:
θ=Body Trunk absolute angle.
G=Angular rate measured by gyroscope.
$t_0$=Initial time
$\theta(t_0)$=Initial trunk tilt value in $t=t_0$.

Figure 16:
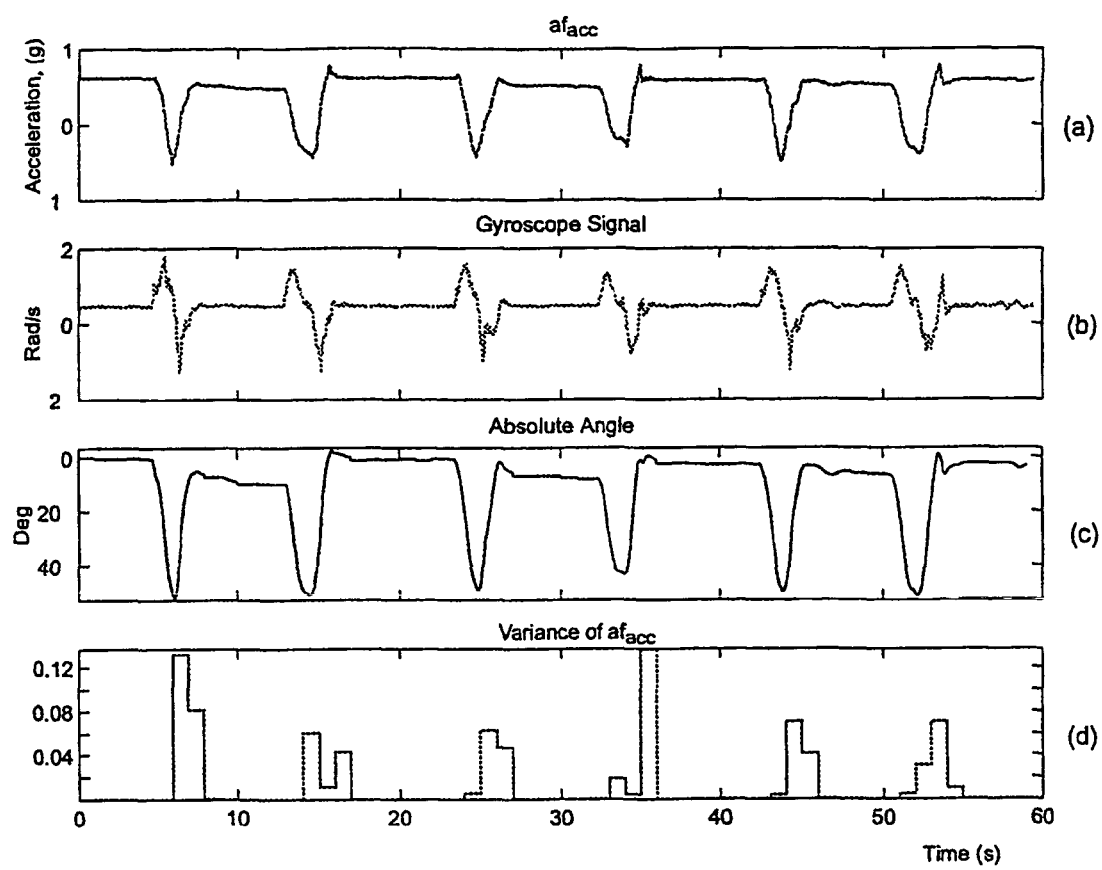
FIG. 16 shows a first trunk tilt estimation
Figure 17:
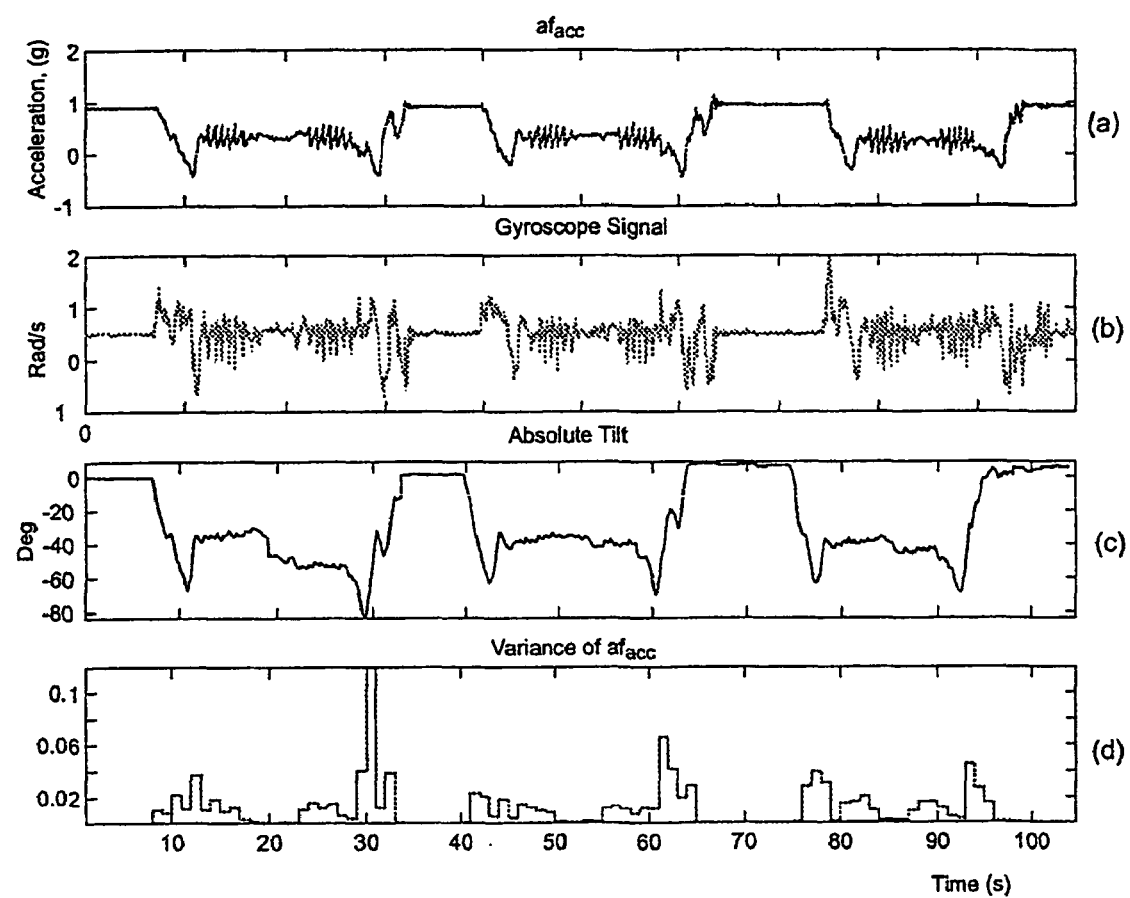
FIG. 17 shows another trunk tilt estimation

It is clear that if there is one value of absolute tilt in any time, the absolute trunk tilt can be calculated over the time from above equation too. For finding of this initial value the mentioned method for calculating of 'θ' by frontal accelerometer is used. Then with combination of an accelerometer and a gyroscope, which are placed on the body trunk and the above method, absolute trunk tilt can be estimated. Two sample of absolute trunk tilt estimation for two different activities have been shown in FIGS. 16 and 17 . . . $af_{acc}$ and trunk angular rate measured by gyroscope have been shown on FIGS. 16(a) and (b). FIGS. 16(c) and (d) show the absolute trunk tilt and variance of $af_{acc}$ respectively, calculated by this method during sit-stand and stand-sit transition FIG. 17 shows the same parameters on FIG. 16 for lying, walking and getting up from the bed activities.

In addition, by using a vertical accelerometer the value of inertial acceleration can be estimated as follow:

$$av_{acc.} = (a_v+g)\cos\theta - a_f\sin\theta \quad (3)$$

Where:
$av_{acc.}$=Measured signal by vertical accelerometer.

Knowing the $a_v$ is useful for calculating of vertical velocity and displacement and knowing $a_f$ is useful for calculating of frontal velocity and displacement.

It should be understood that this invention is not limited to the examples or embodiments herein disclosed but comprises all modified forms as come with in the scope of the following claims.

The invention claimed is:

1. A body movement monitoring system comprising:
a sensor to be attached to a trunk of a subject,
processing means for deriving information from said sensor,
display means for displaying said information to an operator,
wherein said system includes means for determining the time of postural transition by calculating a trunk tilt θ by integrating an angular rate signal measured by said sensor, calculating sin θ, and obtaining the postural transition corresponding to the minimum peak of sin θ.

2. A monitoring system according to claim 1 wherein the sensor comprises a miniature gyroscope.

3. A monitoring system according to claim 1 wherein said system includes means to determine the duration and the type of postural transition.

4. A monitoring system according to claim 1 comprising an alarm which is activated when the quality of postural transition is behind a threshold.

5. A monitoring system according to claim 1 comprising furthermore a vertical accelerometer.

6. A monitoring system according to claim 5 comprising furthermore a forward accelerometer.

7. A method for measuring the time of postural transition comprising:
  attaching a sensor to a trunk of a subject,
  processing information from said sensor,
  displaying said information to an operator,
  determining the time when a postural transition occurs, wherein a trunk tilt $\theta$ is first calculated by integrating an angular rate signal measured by said sensor, $\sin \theta$ is then calculated, and the postural transition corresponds to the minimum peak of $\sin \theta$.

8. A method according to claim 7 wherein a duration of postural transition is determined based on the duration between the maximum peaks of $\sin \theta$ which occur before and after the instant of postural transition.

9. A method according to claim 7 wherein the method further determines a duration and a type of postural transition and wherein falling risk is determined by a combination of three parameters comprising an average and standard deviation of transition duration and an occurrence of abnormal successive transition.

10. A method according to claim 7 further comprising monitoring and measuring physical activity via a vertical accelerometer.

* * * * *